United States Patent
Morrow

(10) Patent No.: US 6,316,845 B1
(45) Date of Patent: Nov. 13, 2001

(54) BATTERY POWERED AC ELECTROMAGNETIC YOKE FOR MAGNETIC PARTICLE INSPECTION

(75) Inventor: Richard A. Morrow, Tarpon Springs, FL (US)

(73) Assignee: Parker Research Corporation, Dunedin, FL (US)

( * ) Notice: Subject to any disclaimer, the term of this patent is extended or adjusted under 35 U.S.C. 154(b) by 0 days.

(21) Appl. No.: 09/434,943

(22) Filed: Nov. 5, 1999

(51) Int. Cl.[7] .................................................. H01F 13/00
(52) U.S. Cl. ............................ 307/66; 307/87; 361/267
(58) Field of Search .................................. 324/236–238; 361/144, 145, 149–151, 267; 307/66, 85–87; 335/284–295

(56) References Cited

U.S. PATENT DOCUMENTS

| | | |
|---|---|---|
| 2,110,759 | 3/1938 | DeForest . |
| 2,136,375 | 11/1938 | DeForest . |
| 2,158,409 | 5/1939 | DeForest et al. . |
| 2,447,899 | 8/1948 | Coon . |
| 2,930,972 | 3/1960 | Taylor . |
| 3,034,021 | 5/1962 | Callihan . |
| 3,252,074 | 5/1966 | Maine . |
| 3,590,367 | 6/1971 | Ptomey et al. . |
| 3,596,143 | 7/1971 | Gruetzmacher et al. . |
| 3,855,530 | 12/1974 | Fuji et al. . |
| 4,058,762 | 11/1977 | Holt et al. . |
| 4,523,250 * | 6/1985 | Bacchiere et al. ............... 361/145 |
| 4,645,947 | 2/1987 | Prak . |
| 4,950,989 | 8/1990 | Jones . |
| 5,122,743 | 6/1992 | Blakeley et al. . |
| 5,311,126 * | 5/1994 | Mittleman et al. . |
| 5,341,263 * | 8/1994 | McGreevy et al. ................ 360/128 |
| 5,686,850 | 11/1997 | Takaki et al. . |
| 5,729,447 | 3/1998 | Albach et al. . |

FOREIGN PATENT DOCUMENTS

| | | | |
|---|---|---|---|
| 3181012 * | 8/1991 | (JP) | ........................... G11B/05/465 |

* cited by examiner

Primary Examiner—Fritz Fleming
(74) Attorney, Agent, or Firm—Ronald E. Smith; Smith & Hopen, P.A.

(57) ABSTRACT

A portable, battery-operated AC electromagnetic yoke for detecting surface defects in ferrous materials by employing an AC magnetic field. The yoke includes a circuit that produces a quasi AC square wave voltage. The resulting AC magnetic field is the required inspection method of common practice and is capable of demagnetizing upon completion of inspection. A first bank of batteries supplies approximately sixty volts positive DC and a second bank of batteries supplies approximately sixty volts negative DC to power transistors that are in electrical communication with the yoke. Logic circuitry is employed to switch the respective banks of batteries on and off to simulate an AC circuit. The logic circuit includes a clock for generating pulses that are fed to a phase splitter circuit and to a delay and pulse shaping circuit. The respective outputs of those circuits are fed to logic gates that are in electrical communication with a voltage level shifting circuit that triggers the power drivers. A plurality of power resistors in conjunction with the inductor in the yoke provides the proper time constant for the magnetizing current to reach a large enough value to provide sufficient magnetic force to detect the surface defects, demagnetize, and lift ten pounds of ferrous material.

16 Claims, 6 Drawing Sheets

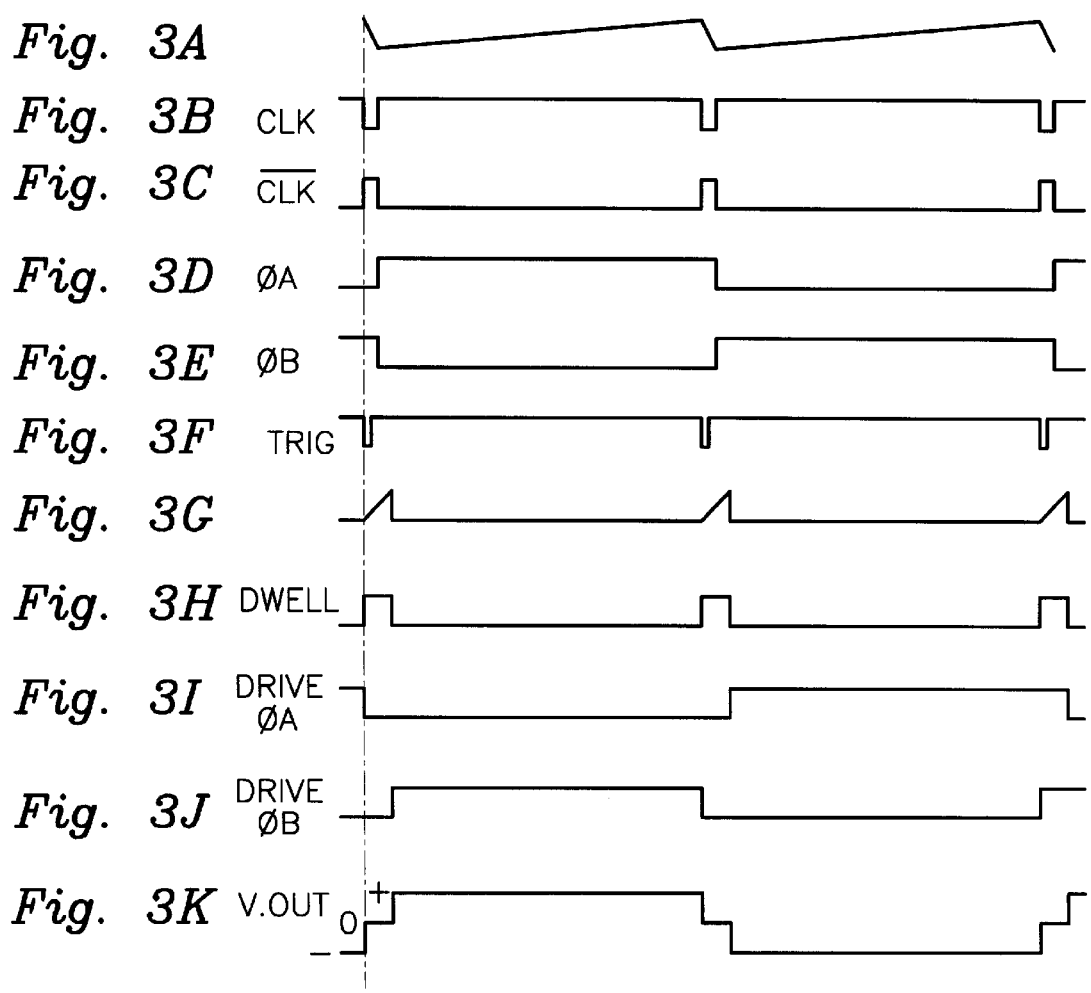

BATTERY POWERED AC ELECTROMAGNETIC YOKE FOR MAGNETIC PARTICLE INSPECTION

BACKGROUND OF THE INVENTION

1. Field of the invention

This invention relates, generally, to a portable, battery-operated AC electromagnetic yoke for detecting surface defects in ferrous materials. More particularly, it relates to a circuit that produces a quasi AC square wave voltage so that the inspection is performed by the required method of common practice and is capable of demagnetizing upon completion of inspection.

2. Description of the prior art

There are a number of patents on AC electromagnetic yokes having utility in the field of magnetic particle inspection, but most are reliant upon common 115/230VAC alternating line current and therefore cannot be used in many field applications where 115/230VAC line current is not available or where there may be safety concerns associated with 115/230VAC line current. For example, see U.S. Pat. No. 2,136,375 to DeForest.

There are also patents on battery-powered electromagnetic yokes suitable for use in the field, but they produce DC currents which are not acceptable for most inspection requirements of common practice. Accordingly, these devices lack utility in applications where the inspected part must be in a demagnetized state at the completion of the inspection. U.S. Pat. No. 4,950,989 to Jones discloses a magnetic particle inspector that can use AC or half-wave DC.

Circuits for changing DC to AC, known as inverter circuits, are well known. However, electromagnetic yokes for magnetic particle inspection have inductors that produce large inductances and the power requirements of such yokes are high. Thus, common inverter circuits fail to provide the needed fill, square wave that closely emulates an AC wave.

U.S. Pat. No. 2,447,899 is believed to be the most relevant prior art patent because it discloses an electromagnetic particle inspector unit having a battery-powered circuit for producing an emulated AC voltage. However, the emulated AC voltage is not a true square wave and the device disclosed in that patent cannot generate a magnetic field capable of lifting at least ten pounds. Applicable inspection specifications require that the AC magnetic field generated by the inspection device have a strength sufficient to lift that amount of weight.

What is needed, then, is an electromagnetic particle inspection yoke having a battery-powered circuit that produces a true square wave voltage to provide highly reliable detection of defects in inspected parts. The needed yoke should generate a magnetic field strength capable of lifting at least ten pounds and should be capable of leaving the inspected part in a demagnetized condition.

However, it was not obvious to those of ordinary skill in this art how the needed yoke could be provided, in view of the art considered as a whole at the time the present invention was made.

SUMMARY OF THE INVENTION

The long-standing but heretofore unfulfilled need for an innovation that overcomes the limitations of the prior art is now met by a new, useful, and nonobvious invention. The present invention includes an electromagnetic yoke for magnetic particle inspection. A first battery means supplies a predetermined positive voltage to the electromagnetic yoke and a second battery means supplies a predetermined negative voltage thereto. A switching means switches from the first battery means to the second battery means and back to the first battery means to complete a cycle, continuously performing the switching at a predetermined number of cycles per second. The result is a square waveform that emulates a sinusoidal alternating current waveform so that a ferrous article under inspection is demagnetized at the conclusion of the inspection. The first battery means supplies about sixty positive volts of direct current and the second battery means supplies about sixty negative volts of direct current.

The switching means includes a first clock means that provides a clock pulse having a predetermined frequency for developing the square waveform. The switching means further includes phase splitting means that splits the clock pulse into a first square wave and a second square wave that is shifted in phase one hundred eighty degrees relative to the first square wave. The first and second square waves have a frequency that is one-half the predetermined frequency of the clock pulse. The switching means further includes a pulse shaping means that is triggered on the second square wave and which produces a pulse shaping trigger pulse.

A delay means produces a dwell time pulse that determines the dwell time for the waveform applied to the electromagnetic yoke, the delay means is a second clock means that is triggered by the pulse-shaping trigger pulse. The dwell time pulse is timed so that the dwell time pulse begins before the first and second square waves begin and ends after the first and second square waves have begun.

The switching means further includes a first drive transistor means dedicated to switching the positive DC voltage and a second drive transistor means dedicated to switching the negative DC voltage. The first drive transistor means preferably includes a pair of field effect transistors connected in parallel to one another and the second drive transistor means includes a pair of field effect transistors connected in parallel to one another. The dwell pulse determines the length of time that the first and second transistor means are turned off during each cycle.

A first low voltage logic circuit is associated with the first drive transistor and a second low voltage logic circuit is associated with the second drive transistor. The first low voltage logic circuit includes a first logic gate for turning the first drive transistor on and off and the second low voltage logic circuit includes a second logic gate for turning the second drive transistor on and off.

The first and second low voltage logic circuits respectively include a first and a second inverter means for placing signals applied to said first and second drive transistors, respectively, in a predetermined phase. A pushbutton switch, when closed, applies a positive voltage to the first and second logic gates; this removes drive signals from the drive transistors, thereby biasing the drive transistors into a non-conducting state.

A first battery monitor means monitors the status of the first battery means and a second battery monitoring means monitors the status of the second battery means. The first and second battery monitor means respectively include an optical isolator for isolating high positive and negative voltages produced by the first and second battery means from the first and second low voltage logic circuits.

It is a primary object of this invention to provide a battery-operated electromagnetic yoke for magnetic particle inspection having an emulated AC voltage.

More specific objects are to provide an electromagnetic yoke that generates a magnetic field strength capable of lifting at least ten pounds of a ferrous material and that leaves the inspected article in a demagnetized condition.

These and other important objects, features, and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 3A is a waveform diagram at point 12a of the novel circuit;

FIG. 3B is a waveform diagram at point 12b of the novel circuit;

FIG. 3C is a waveform diagram at point 12c of the novel circuit;

FIG. 3D is a waveform diagram at point 14a of the novel circuit;

FIG. 3E is a waveform diagram at point 14b of the novel circuit;

FIG. 3F is a waveform diagram at point 16a of the novel circuit;

FIG. 3G is a waveform diagram at point 17a of the novel circuit;

FIG. 3H is a waveform diagram at point 17b of the novel circuit;

FIG. 3I is a waveform diagram at point 20a of the novel circuit;

FIG. 3J is a waveform diagram at point 20b of the novel circuit; and

FIG. 3K is a waveform diagram at point 42a of the novel circuit.

DETAILED DESCRIPTION OF THE OF PREFERRED EMBODIMENT

Figure 1:
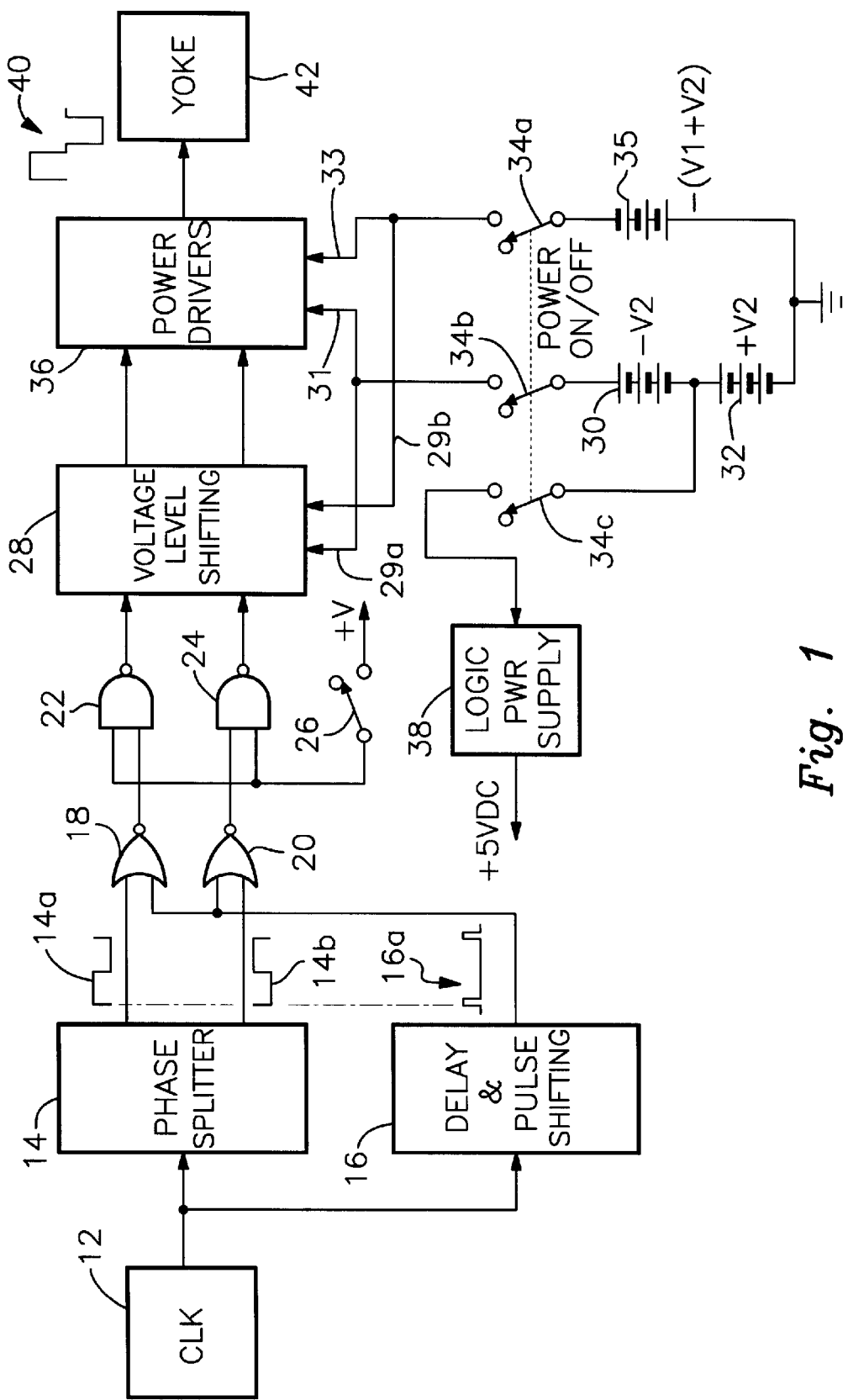
FIG. 1 is a diagrammatic representation of the preferred embodiment of the novel circuitry that produces the novel waveform.

Referring now to FIG. 1, it will there be seen that an exemplary embodiment of the invention is denoted as a whole by the reference numeral 10. It should be understood that FIG. 1 is a simplification of the circuit depicted in FIG. 2 and is provided for the purpose of providing an overview.

Circuit 10 is a digital circuit under the control of clock 12. Each signal generated by clock 12 is fed to the respective inputs of phase splitter means 14 and delay and pulse shaping means 16.

As its name implies, phase splitter means 14 generates two signals that are one hundred eighty degrees apart; the two signals are denoted 14a and 14b. Note that when signal 14a increases in amplitude from zero voltage to a positive voltage (such as five (5) volts), signal 14b decreases from a positive voltage (such as five (5) volts) to zero volts. Both signals remain at their respective positive and zero voltages for the same predetermined amount of time. The cycle then repeats itself.

The signal generated by delay and pulse shifting means 16 is denoted 16a. As best understood by comparing signal 16a with signals 14a and 14b, signal 16a has a positive pulse at three hundred sixty degree intervals.

Signal 14a is applied to a first input of NOR gate 18 and signal 14b is simultaneously applied to a first input of NOR gate 20. Signal 16a is simultaneously applied to the second respective inputs of NOR gates 18 and 20.

The respective outputs of said NOR gates are applied to first inputs of NAND gates 22 and 24, and voltage is applied to the second respective inputs thereof through pushbutton on/off switch 26.

The respective output signals of NAND gates 22 and 24 are applied to voltage shifting means 28. A positive and negative DC voltage is also applied to means 28 as at 29a, 29b by batteries 30, 32, and 35 when switches 34a and 34b are closed.

The output signal of voltage shifting means 28 is applied to respective inputs of power driver circuit 36 and the same positive and negative voltage is applied to a third input 31 of said power driver circuit when switches 34a and 34b are closed. Batteries 30, 32, and 35 supply a positive and negative DC voltage that is applied to inputs 31 and 33 of the power driver circuit when switches 34a and 34b are closed.

Closing switch 34c applies voltage to logic power supply 38 that delivers 5 volts DC to clock 12, phase splitter 14, delay and pulse shifting means 16, NOR gates 18 and 20, NAND gates 22 and 24, and switch means 26. Push button switch 26 is mounted on the yoke assembly and applies the magnetizing current to the yoke when it is depressed. Switch 34 is preferably mounted off the printed circuit board.

The output waveform of the power drivers in circuit 36 is denoted 40 and that waveform is applied to electromagnetic particle inspection yoke 42 which has a conventional mechanical structure and includes inductor 43.

Waveform 40 has a peak-to-peak voltage of approximately one hundred twenty volts because its positive and negative peaks have an amplitude of approximately sixty volts. As diagrammatically depicted, it begins a cycle by reaching positive amplitude and maintaining that amplitude steadily for a first predetermined amount of time. It then goes to zero and after a short delay reaches a negative value, equal in amplitude to the positive value. It maintains that negative value for a predetermined amount of time equal to the first predetermined amount of time, returns to zero, and after a short delay the cycle is repeated.

In the preferred embodiment, each bank of batteries provides a positive DC voltage of about 60 volts (five (5) batteries of about 12.7 volts each) and a negative DC voltage of about 60 volts (also five (5) batteries of about 12.7 volts each). This produces in yoke 42 a magnetic field having a strength sufficient to lift ten pounds.

FIGS. 2A–D depict the preferred circuit in greater detail. Each signal ground is denoted by the reference numeral 11.

Figure 2A:
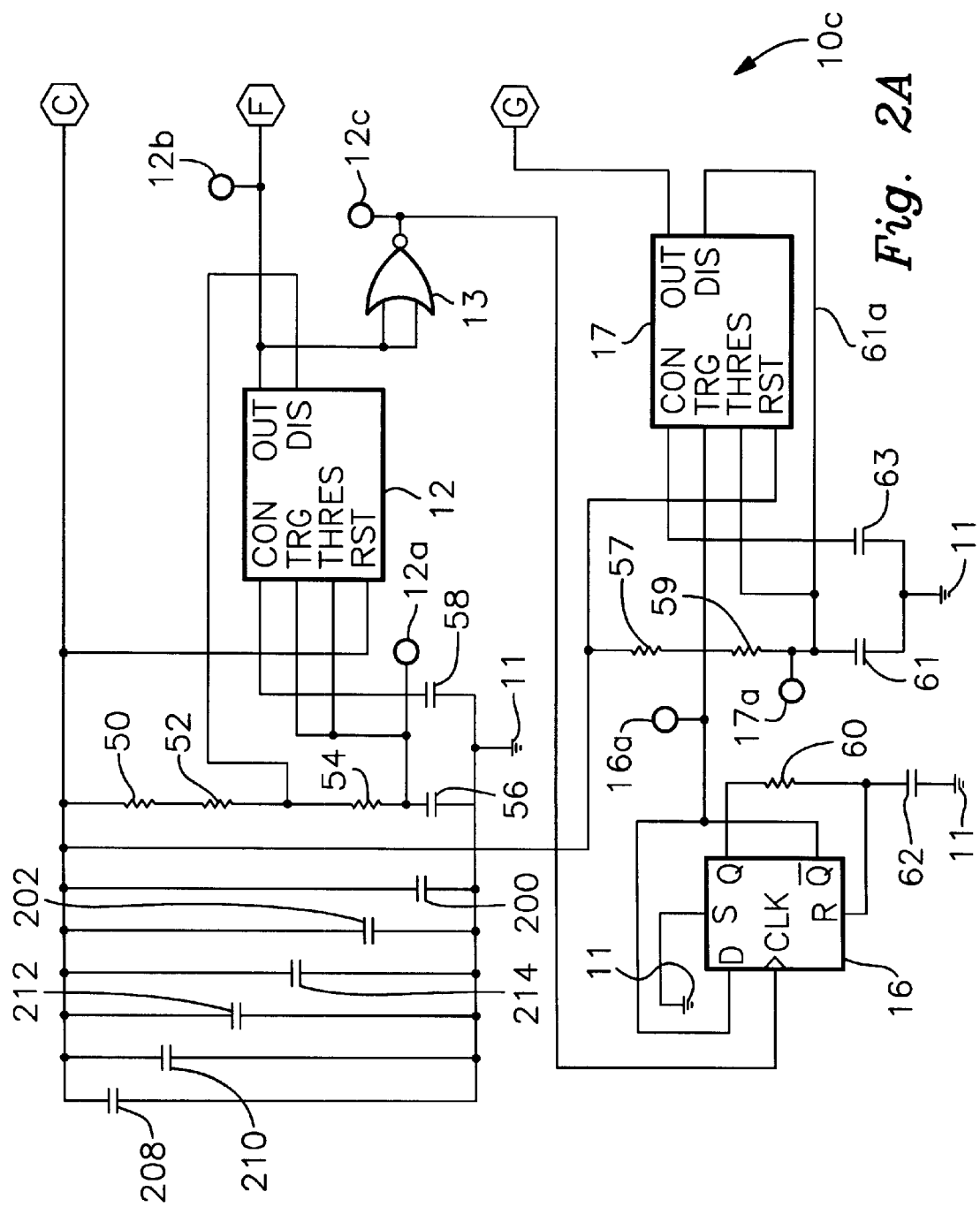
FIGS. 2A–D are a detailed circuit diagram of the preferred embodiment.
Figure 2B:
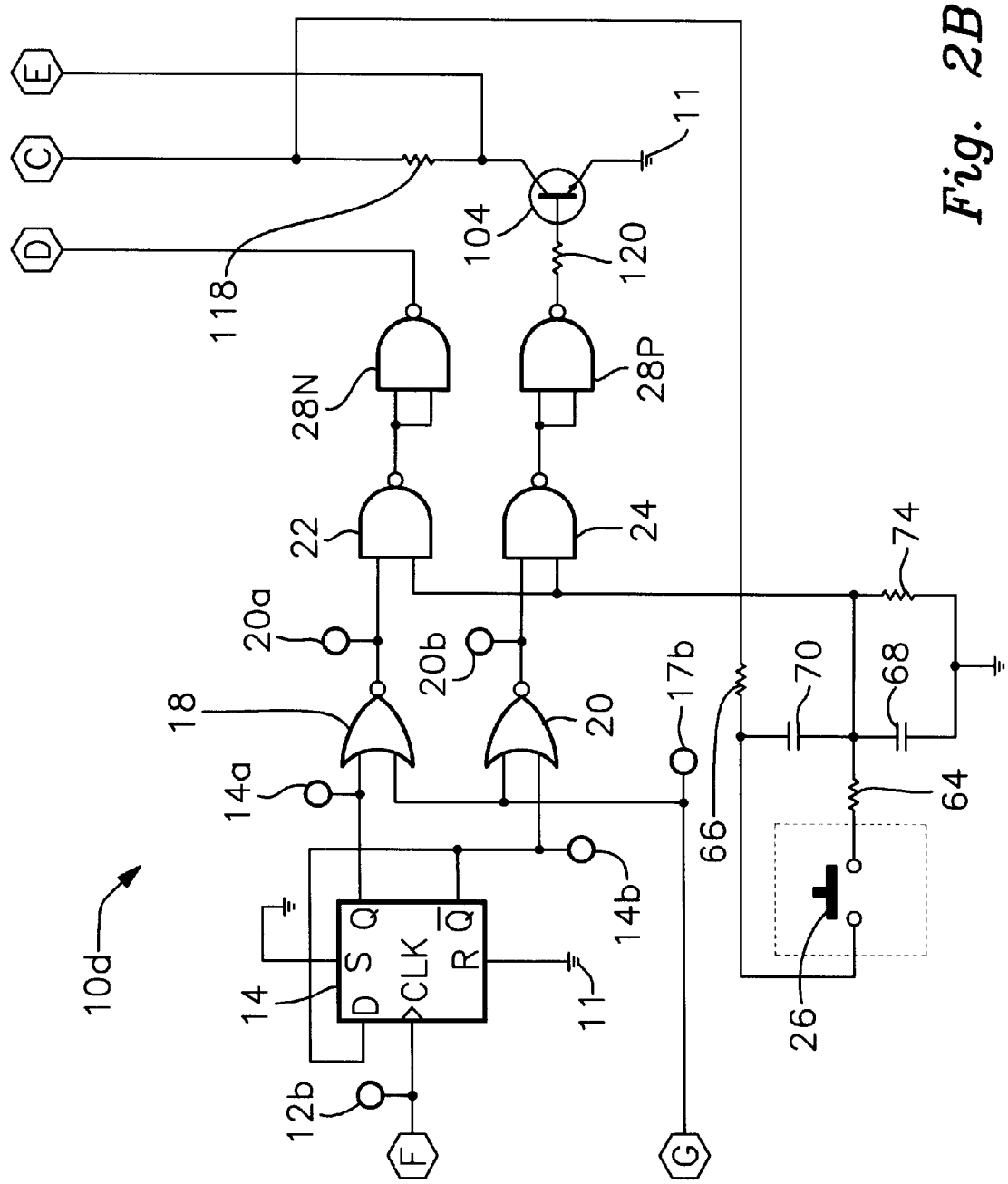
Figure 2C:
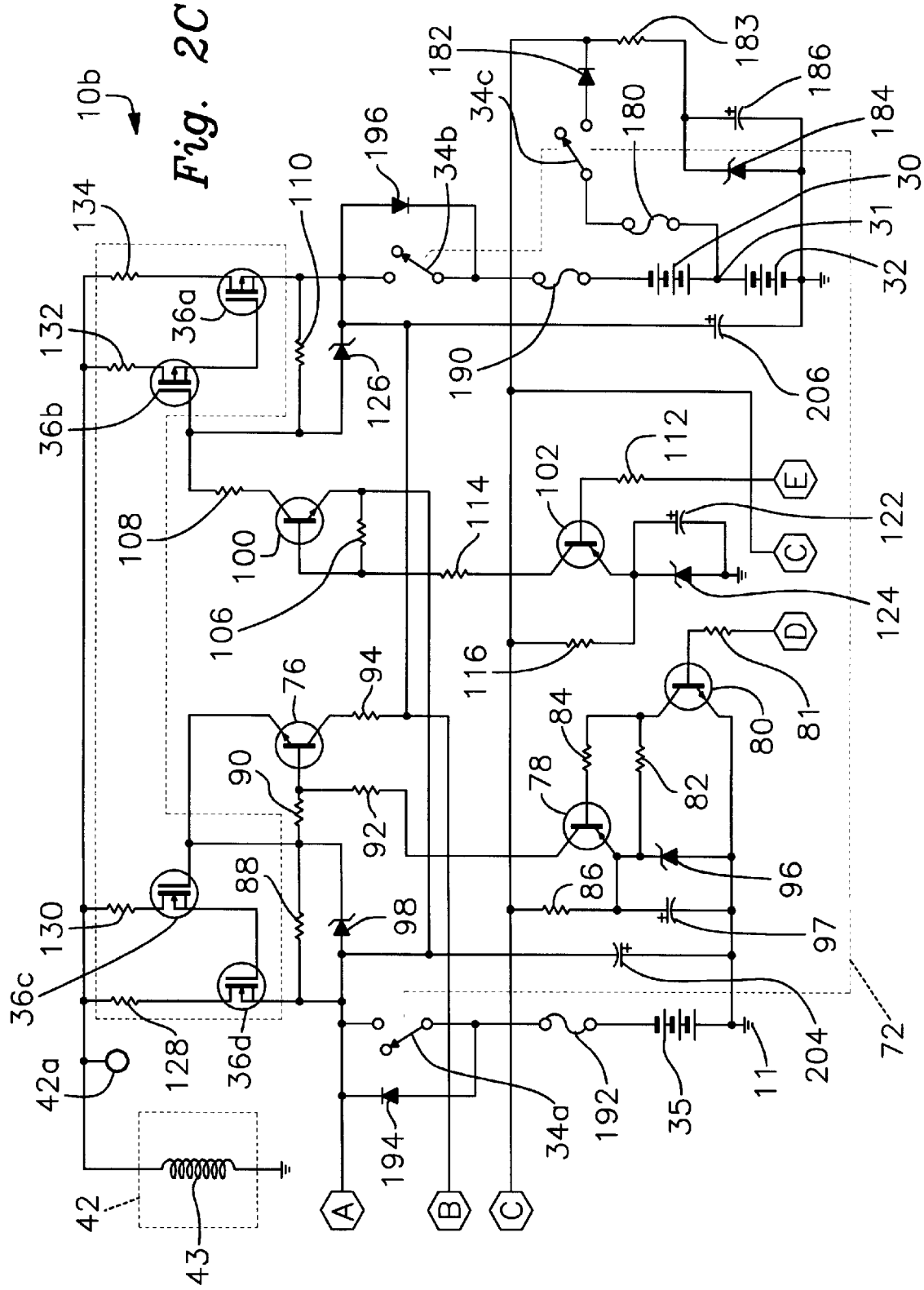

Referring first to FIG. 2A, clock 12 is an astable multivibrator that provides the master timing pulse to develop the yoke drive voltage waveform. Resistors 50, 52, 54, and capacitor 56 determine the operating frequency of the yoke voltage. Capacitor 56 is charged through resistors 50, 52, and 54 until the threshold voltage of clock 12 is exceeded. Capacitor 56 is then discharged through resistor 54. The width of the timing pulse is determined by the time required to discharge said capacitor 56. Capacitor 58 is a noise suppression capacitor.

The waveform at clock input 12a appears in FIG. 3A, the output waveform at 12b is depicted in FIG. 3B, and the output waveform 12c after inversion thereof by NOR gate 13 is depicted in FIG. 3C.

Monostable multivibrator 14 (FIG. 2B) performs a phase splitting function. It triggers on the rising edge of the clock pulse, resulting in two square waves shifted in phase 180° from one another at one-half the frequency of the clock pulse. The respective waveforms 14a, 14b at the output of phase splitting means 14 are depicted in FIGS. 3D and 3E.

As indicated in FIG. 2A, the output of NOR gate 13 is fed to a delay and pulse shaping means that includes monostable multivibrator 16, clock 17, and a timing circuit formed by resistor 60 and capacitor 62. Multivibrator 16 is triggered on the clock pulse shifted 180° by NOR gate 13 (see the waveform diagram of FIG. 3C). The output of multivibrator 16 provides the trigger pulse for clock 17 which produces the pulse that determines the dwell time for the yoke waveform.

Resistors 57, 59 and capacitor 61 form a timing circuit and are in electrical communication with the threshold pin of clock 17. Capacitor 61 charges to a predetermined threshold and turns timer 17 on when it reaches the threshold. The discharge pin of clock 17 is electrically connected to capacitor 61 by conductor 61a.

Capacitor 63 is provided for stability; it keeps noise from falsely triggering clock 17.

The waveform of the trigger pulse as at 16a is depicted in FIG. 3F and the waveform at point 17a is depicted in FIG. 3G. By comparing FIGS. 3D and 3E with FIG. 3G and FIG. 3H, it will be noted that the dwell time pulse starts before the respective starts of square waves of FIGS. 3D and 3E and ends after said respective starts. This eliminates false triggering of drive transistors 36a, 36b, 36C and 36d (FIG. 2C), all of which are preferably field effect transistors (FETs). The length of the dwell time pulse determines the length of time said drive transistors are turned off during each cycle. This ensures that P channel FETs 36a, 36b and N channel FETs 36c, 36d will not be on at the same time so that positive battery supply 30, 32 and negative battery supply 35 are not shorted together.

During the time interval where both the P channel transistors 36a, 36b and the N channel transistors 36c, 36d are turned off, the magnetic field around inductor 43 of yoke 42 (FIG. 2C) collapses and returns energy to the batteries.

The dwell time is preselected so that current will have sufficient time within which to build up during the time the transistors are on so that the electromagnetic field is sufficiently strong to lift a ten pound weight. If the dwell time is too long, the current will have insufficient time within which to build up.

NAND gates 18 and 20 (FIG. 2B) perform the switching function of turning drive transistors 36a–d on and off. Pushing push button switch 26 FIG. 2B) applies a positive voltage to the inputs of NAND gates 22 and 24; this removes the drive signals and biases the drive transistors into their non-conductive state, i.e., into their "off" state.

Resistors 64, 66 and capacitors 68 and 70 are noise filters that eliminate voltage spikes that may appear in the long wires that extend between yoke 42 and the printed circuit board. Resistor 74 biases NAND gates 22 and 24 into their "on" state when pushbutton switch 26 is open.

NAND gate 28N is an inverter that provides the proper phase for drive transistors 36c and 36d. Transistors 76, 78, and 80 (FIG. 2C) convert the five volt logic signals to the negative approximately sixty volt drive voltage for drive transistors 36c and 36d. Resistors 82, 84, 86, 88, 90, 92, 94, and zener diode 96 provide bias for transistors 76, 78, and 80. Filter capacitor 97 lowers noise and prevents false triggering of transistors 78, 80. Resistor 81 limits current to the base of transistor 80.

Zener diode 98 limits the base to source voltage of drive transistors 36c, 36d to negative twelve volts.

NAND gate 28P (FIG. 2B) is an inverter that provides the proper phase for drive transistors 36a and 36b. Transistors 100, 102, and 104 convert the five volt logic signals to the positive approximately sixty volt drive voltage for drive transistors 36a, 36b. Resistors 106, 108, 110, 112, 114, 116, 118, 120, capacitor 122, and zener diode 124 (FIG. 2C) provide bias for said transistors 100, 102, and 104. Zener diode 126 limits the base to source voltage of drive transistors 36a, 36b to positive twelve volts.

Drive transistors 36c, 36d, connected to one another in parallel, perform the function of switching the negative battery current through the coil 43 of yoke 42. Power resistors 128 and 130 provide the proper time constant that allows the current to increase at a rate that is fast enough to provide sufficient magnetic force to lift a ten pound ferrous load. More particularly, these power resistors, in conjunction with inductor 43 of yoke 42, provide the proper time constant for the magnetizing current to reach a large enough value to provide sufficient magnetic force to detect surface defects, demagnetize, and lift ten pounds of ferrous material.

Drive transistors 36a, 36b, connected to one another in parallel, perform the function of switching the positive battery current through coil 43 of yoke 42. Power resistors 132 and 134 provide the proper time constant that allows the current to increase at a rate fast enough to provide sufficient magnetic force to lift a ten pound ferrous load. More particularly, these power resistors, in conjunction with inductor 43 of yoke 42, provide the proper time constant for the magnetizing current to reach a large enough value to provide sufficient magnetic force to detect surface defects, demagnetize, and lift ten pounds of ferrous material.

Power resistors 128, 130, 132, and 134, in addition to providing the proper time constant as aforesaid, also prevent current from increasing beyond predetermined current specifications when the yoke is removed from the ferrous material being inspected.

Figure 2D:
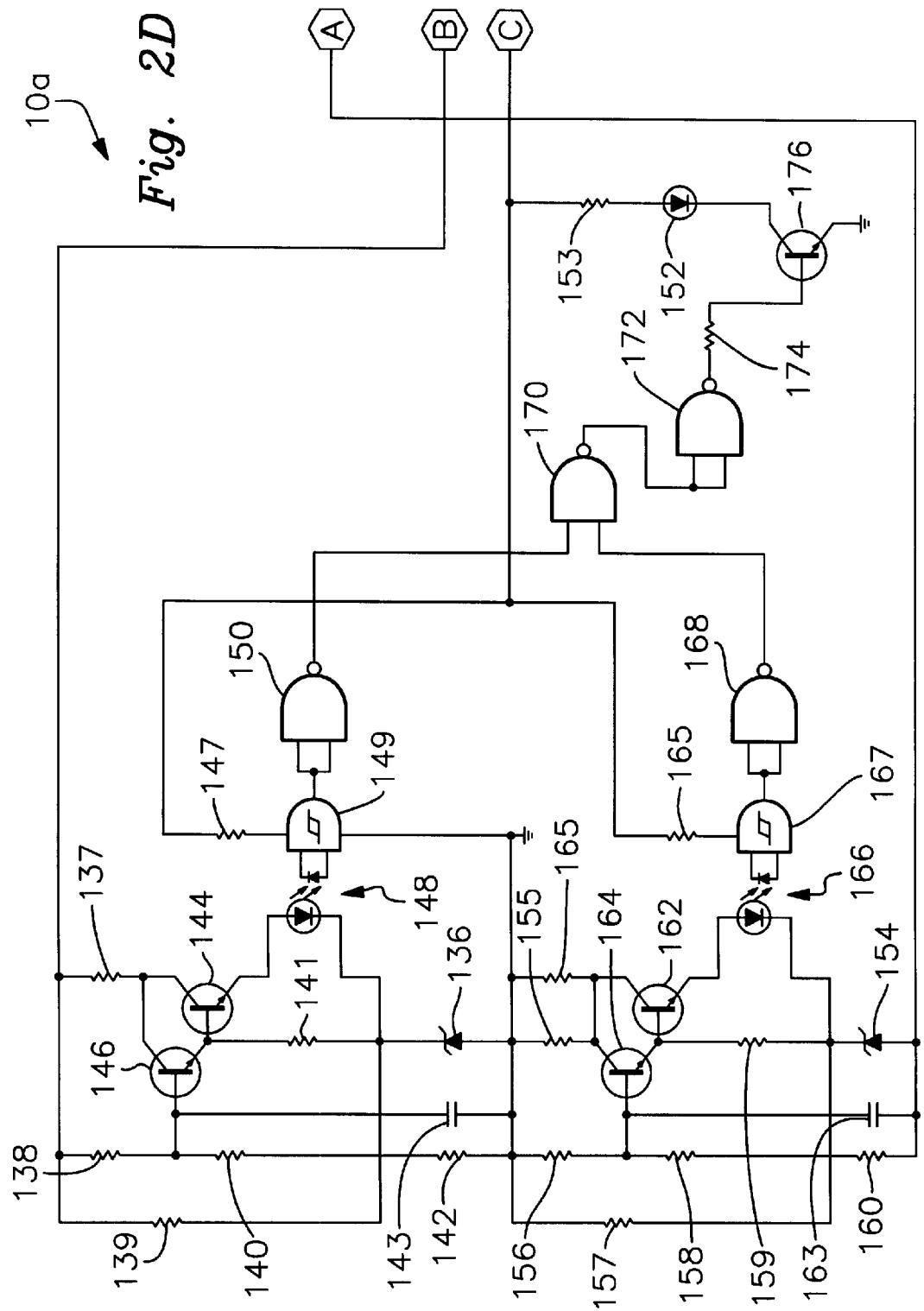

Turning now to the circuitry for the battery voltage monitor of this invention, depicted in FIG. 2D, zener diode 136 establishes the reference voltage for the positive battery voltage monitor. Voltage divider resistors 138, 140, and 142 provide the voltage signal from the battery to amplifiers 144 and 146 to compare with said reference voltage. Load resistor 137 develops the signal amplified by transistor 146, resistor 139 biases zener diode 136, and impedance-lowering resistor 141 stabilizes the base of transistor 144 against temperature variations. Capacitor 143 is a filter capacitor.

Optical isolator 148, which includes Schmitt trigger 149, isolates the high positive battery voltage from the five volt logic voltage. Resistor 147 provides a load for said Schmidt trigger 149.

The positive and negative monitor signals from optical isolator 148 are fed to the inputs of NAND gate 150 to AND said signals together and to invert the output. Light-emitting diode 152 is a green LED that, when lit, indicates that the battery voltages are at the proper levels for operation of yoke 42.

Similarly, zener diode 154 establishes the reference voltage for the negative battery voltage monitor. Voltage divider resistors 156, 158, and 160 provide the voltage signal from the battery to amplifiers 162 and 164 to compare with said reference voltage.

Load resistor 155 develops the signal amplified by transistor 164, resistor 157 biases zener diode 154, and impedance-lowering resistor 159 stabilizes the base of transistor 164 against temperature variations. Capacitor 163 is a filter capacitor.

Optical isolator 166, which includes Schmitt trigger 167, isolates the high negative battery voltage from the five volt logic voltage. Resistor 165 provides a load for said Schmidt trigger 167.

The positive and negative monitor signals from optical isolator 166 are fed to the inputs of NAND gate 168 to AND said signals together and to invert the output. NAND gate 168 ANDs the positive and negative monitor signals from optical isolator 166 together and inverts the output.

The respective output signals of NAND gates 150 and 168 are fed into the inputs of NAND gate 170 and the output signal of NAND gate 170 is fed to the inputs of NAND gate 172 to invert said signal. The output signal of NAND gate 172 is fed to green LED 152 through biasing resistor 174 and amplifier 176. Resistor 153 limits the current through LED 152 when transistor 176 is conducting.

The low voltage logic power supply circuit is in electrical communication with DC voltage between batteries 30, 32 as at 31, and fuse 180 protects said circuit. Closing switch 34c completes the circuit through diode 182 and current limiting resistor 183. Zener diode 184 is a voltage regulator and capacitor 186 performs a filtering, i.e., noise suppression function.

Power is delivered to yoke 42 from batteries 30, 32 (approximately sixty volts positive) and 35 (60 volts negative) through fuses 190, 192, respectively when switches 34b and 34a are closed. Diodes 194 and 196 are in parallel with respect to switches 34a, 34b, respectively.

Filter capacitors 200, 202, 204, 206, 208, 210, 212, and 214 (FIG. 2A) are positioned throughout the circuit as depicted and perform the function their name expresses.

The following list of elements and values or part numbers is provided to eliminate any need for experimentation when constructing the novel circuit. All values are believed to be optimal or nearly so. All resistances are in Ohms and all resistors (R) are ⅛ watt unless otherwise specified. Capacitors and transistors are abbreviated as "C" and "T" respectively.

| Part | Value or Part Number |
| --- | --- |
| Clocks 12 and 17 | NE556 |
| NOR gates 13, 18, and 20 | CD4001BE |
| Multivibrators 14 and 16 | CD4013BE |
| NAND gates 22, 24, 28N, 28P, 150, 168, 170, and 172 | CD4011BE |
| Battery 30 | 36 volts DC |
| Battery 32 | 24 volts DC |
| Battery 35 | 60 volts DC |
| FETs 36a, 36b | IRF 9640 |
| FETs 36c, 36d | IRF 630 |
| R 50 | 510K |
| R 52 | 39K |
| R 54 | 16K |
| C 56, 61, 62 | .022 μfd |
| C 58, 63, 68, 70 | .01 μfd |

-continued

| Part | Value or Part Number |
| --- | --- |
| R 60 | 3.3K |
| R 64, 66 | 100 |
| R 74, 84, 90, 106, 116, 118, 140, 147, 158, 174 | 10k |
| T 76, 80, 100, 104 | 2N6517 |
| T 78, 82, 102 | 2N6520 |
| R 86, 88, 110 | 1.5K, ¼ watt |
| R 92 | 27K |
| R 94 | 22K, 1 watt |
| Zener diodes 96, 98 | IN5242B, 12 volts |
| C 97 | 33 μfd, 100 volts |
| R 108 | 15K, 1 watt |
| R 112, 120 | 47k |
| R 114 | 27k |
| C 122, 186 | 22 μfd, 25 volts |
| Zener diode 124 | IN5222B, 2.5 volts |
| Zener diode 126, 136, 154 | IN5242B, 12 volts |
| R 128, 130, 132, 134 | 10 Ohms, 50 watts |
| R 137, 155 | 9.1K, ¼ watt |
| R 138, 156 | 51K |
| R 139, 157 | 20K, ¼ watt |
| R 141, 159 | 20K |
| R 142, 160 | 5.1K |
| T 144, 146, 162, 164, 176 | 2N5551 |
| R 153 | 4.7K, ¼ watt |
| Fuse 180 | 100ma |
| Diode 182, 194, 196 | IN4004 |
| R 183 | 1.2K, ½ watt |
| Zener diode 184 | IN5231B, 5 volts |
| Fuse 192 | 8 amps |
| C 143, 163 200, 202, 208, 210, 212, 214 | .1 μfd |
| C 204 | 33 μfd, 100 volts |

This invention represents a major breakthrough in the art of battery-operated electromagnetic yokes for magnetic particle inspection. Being drawn to a pioneering invention, the claims that follow are entitled, as a matter of law, to broad interpretation to protect the heart or essence of the invention from piracy.

It will thus be seen that the objects set forth above, and those made apparent from the foregoing description, are efficiently attained. Since certain changes may be made in the foregoing construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An electromagnetic yoke for electromagnetic particle inspection, comprising:

a first battery means for supplying a predetermined positive voltage to said electromagnetic yoke;

a second battery means for supplying a predetermined negative voltage to said electromagnetic yoke;

switching means for switching from said first battery means to said second battery means and back to said first battery means to complete a cycle, said switching means continuously performing said switching at a predetermined number of cycles per second;

said switching means including a first drive transistor means dedicated to switching said positive DC voltage on and off and a second drive transistor means dedicated to switching said negative DC voltage on and off; and a clock means for providing a timing pulse of predetermined frequency that controls operation of said first and second drive transistor means;

whereby a square waveform that emulates a sinusoidal alternating current waveform is produced;

whereby a ferrous article under inspection is demagnetized at the conclusion of the inspection.

2. The electromagnetic yoke of claim 1, further comprising a plurality of power resistors, in conjunction with an inductor of said yoke, for providing a time constant for a magnetizing current to reach a large enough value to provide sufficient magnetic force to detect surface defects, demagnetize, and lift at least ten pounds of ferrous material.

3. The electromagnetic yoke of claim 2, wherein said power resistors prevent current from increasing beyond predetermined current specifications when said yoke is removed from a ferrous material being inspected.

4. The electromagnetic yoke of claim 1, wherein said first battery means supplies about sixty positive volts of direct current.

5. The electromagnetic yoke of claim 1, wherein said second battery means supplies about sixty negative volts of direct current.

6. The electromagnetic yoke of claim 1, wherein said switching means further comprises phase splitting means that splits said timing pulse into a first square wave and a second square wave that is shifted in phase one hundred eighty degrees relative to said first square wave, said first and second square waves having a frequency that is one-half said predetermined frequency of said timing pulse.

7. The electromagnetic yoke of claim 6, wherein said switching means further comprises pulse shaping means that is triggered on said second square wave and which produces a pulse shaping trigger pulse.

8. The electromagnetic yoke of claim 7, wherein said switching means further comprises a delay means that produces a dwell time pulse that determines the dwell time for the waveform applied to said electromagnetic yoke.

9. The electromagnetic yoke of claim 8, wherein said delay means is a second clock means that is triggered by said pulse shaping trigger pulse.

10. The electromagnetic yoke of claim 9, wherein said dwell time pulse is timed so that said dwell time pulse begins before said first and second square waves begin and ends after said first and second square waves have begun.

11. The electromagnetic yoke of claim 10, wherein said switching means further comprises a first drive transistor means dedicated to switching said positive DC voltage and a second drive transistor means dedicated to switching said negative DC voltage.

12. The electromagnetic yoke of claim 11, wherein said first drive transistor means includes a pair of field effect transistors connected in parallel to one another and wherein said second drive transistor means includes a pair of field effect transistors connected in parallel to one another, and wherein said dwell pulse determines the length of time that said first and second transistor means are turned off during each cycle.

13. The electromagnetic yoke of claim 1, further comprising a first low voltage logic circuit associated with said first drive transistor and a second low voltage logic circuit associated with said second drive transistor, said first low voltage logic circuit including a first logic gate for turning said first drive transistor on and off and said second low voltage logic circuit including a second logic gate for turning said second drive transistor on and off.

14. The electromagnetic yoke of claim 13, wherein said first and second low voltage circuits respectively include a first and a second inverter means for placing signals applied to said first and second drive transistors, respectively, in a predetermined phase.

15. The electromagnetic yoke of claim 14, further comprising a pushbutton switch that, when closed, applies a positive voltage to said first and second logic gates which removes drive signals from said drive transistors, thereby biasing said drive transistors into a nonconducting state.

16. The electromagnetic yoke of claim 13, further comprising a first battery monitor means for monitoring the status of said first battery means, a second battery monitoring means for monitoring the status of said second battery means, said first and second battery monitor means respectively including an optical isolator for isolating high positive and negative voltages produced by said first and second battery means from said first and second low voltage logic circuits.

\* \* \* \* \*